US00PP31910P2

(12) United States Plant Patent
Egger

(10) Patent No.: US PP31,910 P2
(45) Date of Patent: Jun. 23, 2020

(54) ***HEUCHERA* PLANT NAMED 'ORANGE DELIGHT'**

(50) Latin Name: ***Heuchera* hybrid**
Varietal Denomination: Orange Delight

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/501,732

(22) Filed: May 28, 2019

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 6/80
See application file for complete search history.

*Primary Examiner* — Anne Marie Grunberg
(74) *Attorney, Agent, or Firm* — Klarquist Sparkman, LLP

(57) ABSTRACT

A new and distinct *Heuchera* plant characterized by peach and orange leaf color in summer, khaki-green leaves in fall, red leaves in winter, large leaves with slightly ruffled and rounded lobes, yellow flowers on upright flowering stems, good performance in sun or shade, a large, tall mounding habit with an excellent crown count, and excellent vigor.

1 Drawing Sheet

Botanical denomination: *Heuchera* hybrid.

Variety designation: 'Orange Delight'.

Trademark designation: SIRENS' SONG™ 'Orange Delight'

Cross reference to *Heuchera* 'Dark Night', applied for concurrently having application Ser. No. 16/501,733

Cross reference to *Heuchera* 'Dark 'N' Bright', applied for concurrently having application Ser. No. 16/501,734

BACKGROUND OF THE INVENTION

The present invention relates to a new and distinct cultivar of *Heuchera* given the cultivar name of 'Orange Delight'. *Heuchera* is in the family Saxifragaceae. *Heuchera* 'Orange Delight' originated as a controlled cross using *Heuchera* 'B228-1', a proprietary, unpatented, unnamed seedling as the seed parent, and *Heuchera* 'B226-2', a proprietary, unpatented, unreleased seedling as the pollen parent. These parents are a result of breeding using *Heuchera richardsonii* with proprietary hybrid lines. *Heuchera* 'Orange Delight' was bred to be a hardy landscape plant for sun or shade.

Compared to the seed parent, *Heuchera* 'B228-1', the new cultivar has peach/orange colored leaves and no veil rather than shiny purple and plum colored leaves with a veil.

Compared to the pollen parent, *Heuchera* 'B226-2', the new cultivar has peach/orange colored leaves rather than shiny green leaves.

Compared to *Heuchera* 'TNHEUNEA', U.S. Plant Pat. No. 29,397, the new cultivar has khaki-green colored leaves in late summer and fall rather than red-orange.

This new *Heuchera* is uniquely distinguished by:

1. peach and orange leaf color in summer,
2. khaki-green leaves in fall,
3. red leaves in winter,
4. large leaves with slightly ruffled and rounded lobes,
5. yellow flowers on upright flowering stems, 6. performs well in sun or shade,
7. a large, tall mounding habit with an excellent crown count, and
8. excellent vigor.

This new cultivar has been reproduced only by asexual propagation (tip cuttings and tissue culture using growing tips). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows eight-month-old plants of *Heuchera* 'Orange Delight' growing in one-gallon pots in October in part shade in Canby, Oreg.

FIG. 2 shows a two-year-old plant of *Heuchera* 'Orange Delight' growing in the trial bed in partial shade in June in Canby, Oreg.

FIG. 3 shows one-year-old plants of *Heuchera* 'Orange Delight' growing in the trial bed in full sun in February in Canby, Oreg.

DETAILED PLANT DESCRIPTION

The following is a detailed description of the new *Heuchera* cultivar based on observations taken in mid-August of a seven-month-old specimen growing in a one-gallon pot outside in partial shade in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* 5th edition, 2007.

Plant:

*Form*.—Basal rosette, herbaceous perennial.

*Hardiness*.—USDA Zone 4 to 9.

*Size*.—Grows to 21 cm tall from top of foliage to ground, 41 cm wide.

*Number of crowns*.—About 7.

*Habit*.—Large, mounding.

*Vigor*.—Excellent.

Leaf:

*Type*.—Simple.

*Arrangement*.—Rosette.

*Shape*.—Broadly ovate.

*Number*.—About 80.

*Blade size*.—Grows to 9 cm long and 9 cm wide.

*Venation*.—Palmate.

*Lobing/division*.—4 to 6 very shallow palmate lobes.

*Margins*.—Broadly crenate.

*Apex*.—Mucronulate.

*Base*.—Cordate, semi-overlapping.

*Surface texture*.—Glandular-puberulent on both sides.

*Rugosity*.—Slight.

*Undulation*.—Medium.

*Glossiness*.—Weak.

*Petiole description*.—Grows to 16 cm long and 3 mm wide, glandular hairs; color closest to Greyed Orange 176B.

*Leaf color*.—Older leaves in late summer, topside closest to Green 137B tinted Greyed Brown 199A with veins Grey Brown 199C, bottom side between Greyed Red 182A and Greyed Red 182B with veins closest to Greyed Red 182C; newer leaves in late summer, topside closest to Greyed Purple 183D, veins Greyed Red 181B, bottom side closest to Greyed Purple 185B, veins closest to Greyed Purple 185C; new leaves in summer, topside closest to Red 47A blending to Red 39C, Orange Red 34C, and Yellow Orange 22A, bottom side closest to Red 47C, Orange Red 34D, and Yellow Orange 22B; leaves in winter, between Greyed Purple 187A and Greyed Red 178A, some leaves tinted closest to Greyed Red 182A from sunburn, bottom side closest to Red Purple 71A tinted Red Purple 70A.

Inflorescence:

*Size*.—Grows to 0.5 cm wide and 65 cm long.

*Type*.—Upright thyrse.

*Number of flowers per thyrse*.—About 110.

*Flower density*.—Medium to light.

*Number of thyrse*.—Up to 30.

*Peduncle*.—Grows to 41 cm long and 3 mm wide at base with glandular hairs; closest to Greyed Purple 187A.

*Pedicel*.—Grows to 2.5 mm long, with glandular hairs; Greyed Red 178A.

*Bloom period*.—July to September in Canby, Oreg.

Flower bud:

*Size*.—3 mm wide and 5 mm long.

*Description*.—Glandular-puberulent, ovoid, down facing.

*Color*.—Between Green Yellow 1A and Yellow 4A and Greyed Orange 164B.

Flower:

*Type*.—perfect.

*Shape*.—Campanulate.

*Attitude*.—Side and down facing.

*Size*.—6 mm long and 4 mm wide.

*Corolla description*.—5 petals, each 3 mm long and 1 mm wide, spatulate, margins entire, tip acute, glandular-puberulent on back side, glabrous inside, White NN155 on both sides.

*Calyx description*.—Campanulate, 6 mm long and 4 mm wide; 5 lobes each 3 mm wide and 2 mm long, oblong in shape, back side glandular-puberulent, glabrous inside, tip obtuse, margin entire, new flowers; outside color Green Yellow 1A and Yellow 4A tinted with Greyed Orange 164B on tip measuring 2 mm and bottom measuring 2 mm, older flowers; Green Yellow 1A and Yellow 4A heavily tinted Greyed Purple 183A.

*Stamen description*.—5 in number, filaments 2 mm long, White NN155, anthers 0.4 mm long.

*Pollen*.—Orange N25 B, moderate quantity.

*Pistil description*.—1, 2-beaked, 6 mm long and 2 mm wide, ovary 2 mm long and 2 mm wide, White NN155, style 4 mm long, White NN155.

*Fragrance*.—None.

*Lastingness*.—Each thyrse blooms for about 3 weeks on the plant.

Seed: None seen.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

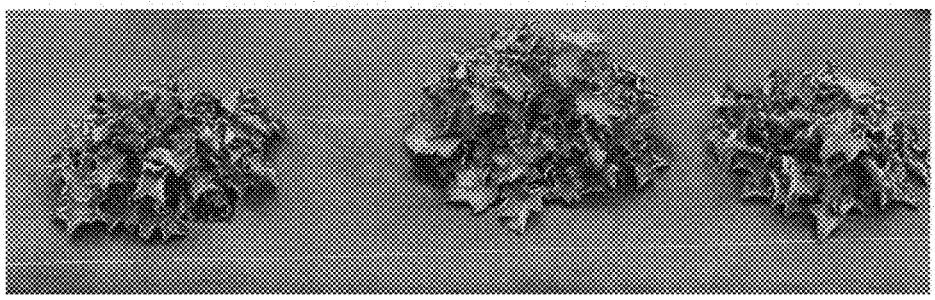

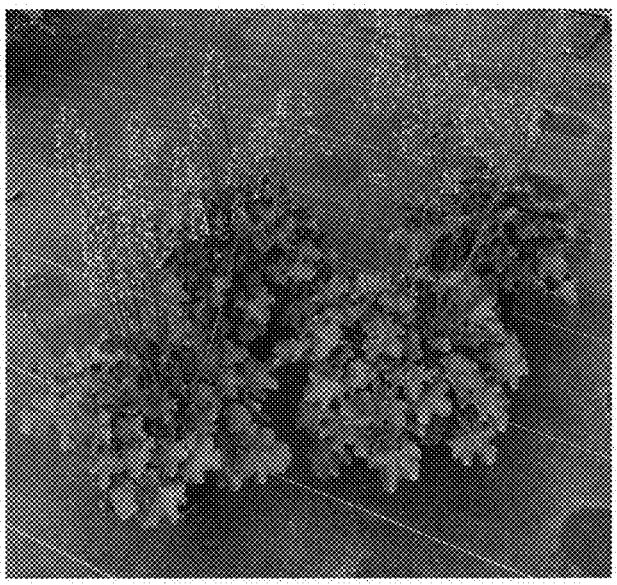
Fig. 1
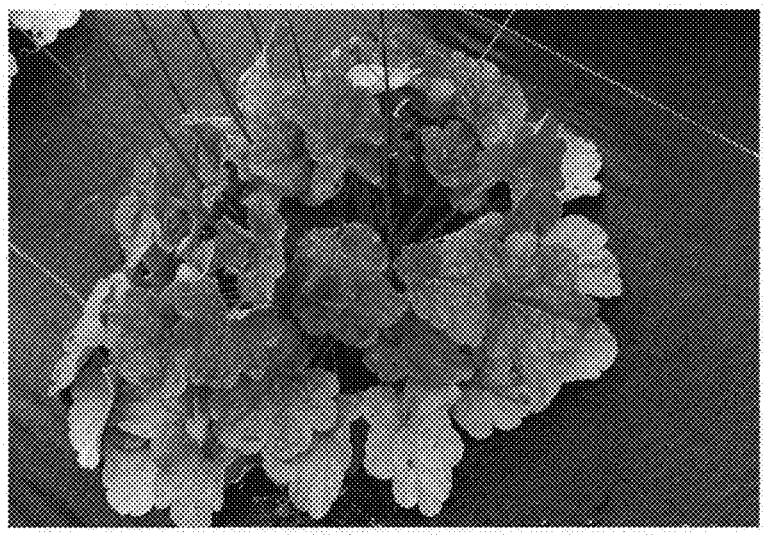
Fig. 2
Fig. 3
Below